US007504635B2

(12) United States Patent
Ramsden (10) Patent No.: US 7,504,635 B2
(45) Date of Patent: Mar. 17, 2009

(54) GAMMA-RAY CAMERA SYSTEM

(75) Inventor: David Ramsden, Southampton (GB)

(73) Assignee: Symetrica Limited, Hampshire (GB)

( * ) Notice: Subject to any disclaimer, the term of this patent is extended or adjusted under 35 U.S.C. 154(b) by 286 days.

(21) Appl. No.: 10/548,985

(22) PCT Filed: Mar. 9, 2004

(86) PCT No.: PCT/GB2004/000982

§ 371 (c)(1),
(2), (4) Date: Sep. 7, 2005

(87) PCT Pub. No.: WO2004/081606

PCT Pub. Date: Sep. 23, 2004

(65) Prior Publication Data

US 2006/0180767 A1     Aug. 17, 2006

(30) Foreign Application Priority Data

Mar. 11, 2003   (GB)   ................................. 0305555.5

(51) Int. Cl.
*G01T 1/20* (2006.01)
(52) U.S. Cl. ........................................................ 250/369
(58) Field of Classification Search ................. 250/369
See application file for complete search history.

(56) References Cited

U.S. PATENT DOCUMENTS 3,944,835 A * 3/1976 Vosburgh .................. 250/487.1
4,839,808 A   6/1989 Koral et al.

(Continued)

FOREIGN PATENT DOCUMENTS

EP   1 004 983   5/2000

(Continued)

OTHER PUBLICATIONS

Anger, Hal O. "Scintillation Camera." *The Review of Scientific Instruments*. vol. 29, No. 1, Jan. 1958.

(Continued)

*Primary Examiner*—David P Porta
*Assistant Examiner*—Kiho Kim
(74) *Attorney, Agent, or Firm*—O'Melveny & Myers LLP (57) ABSTRACT

A scintillator crystal (26) based gamma-ray camera system is described. The gamma-ray camera system includes a spectra processing component for (34) providing improved energy resolution over that seen in conventional gamma-ray camera systems. The spectra processing component operates to deconvolve detector response functions from observed energy spectra on a pixel by pixel basis. The pixel dependent to detector response functions are obtained by a combination of theoretical simulation, and empirical calibration. By deconvolving pixel specific detector response functions, variations in response of a gamma-ray camera system across its image plane can be accounted for. This offers significant improvements in energy resolution and many of the problems associated with conventional gamma-ray camera systems are reduced. For example, the improved energy resolution allows better rejection of photons associated with Compton scattering events occurring in a source being imaged. This is because a narrower energy window filter can be used without rejecting a significant fraction of non-Compton scattered photons. The spectra processing component can be easily implemented with different types of gamma-ray imagers, for example Anger-type cameras, and may also be retroactively fitted to existing gamma-ray camera systems.

15 Claims, 6 Drawing Sheets

U.S. PATENT DOCUMENTS

| | | | |
|---|---|---|---|
| 5,530,248 | A | 6/1996 | Natanzon et al. |
| 5,561,297 | A | 10/1996 | Engdahl |
| 5,576,546 | A * | 11/1996 | Gagnon ..................... 250/369 |
| 5,633,499 | A | 5/1997 | Lim et al. |
| 5,692,507 | A * | 12/1997 | Seppi et al. ................. 600/407 |
| 5,903,008 | A | 5/1999 | Li |
| 6,057,551 | A * | 5/2000 | Tararine ................. 250/363.03 |
| 6,194,715 | B1 * | 2/2001 | Lingren et al. ........... 250/252.1 |
| 6,232,954 | B1 * | 5/2001 | Rozzi ........................ 345/601 |
| 6,369,389 | B1 | 4/2002 | Berlad et al. |
| 6,628,744 | B1 * | 9/2003 | Luhta et al. .................. 378/15 |
| 2001/0001011 | A1 * | 5/2001 | Salb ......................... 378/98.9 |
| 2002/0011571 | A1 * | 1/2002 | Lin et al. .................... 250/366 |
| 2002/0036269 | A1 * | 3/2002 | Shahar et al. ............ 250/370.1 |
| 2002/0051111 | A1 * | 5/2002 | Greene et al. ............... 349/149 |
| 2005/0055174 | A1 * | 3/2005 | David et al. ................. 702/152 |

FOREIGN PATENT DOCUMENTS

| | | |
|---|---|---|
| WO | 98/23973 | 6/1998 |

OTHER PUBLICATIONS

Parnham, K.B., et al. "Development, Design and Performance of a CdZnTe-Based Nuclear Medical Imager." *Proceedings of the SNM 49th Annual Meeting*. vol. 43, No. 5, May 2002.

Meng, L.J. and D. Ramsden, "An Inter-comparison of Three Spectral-Deconvollation Algorithms for Gamma-ray Spectroscopy", IEEE Transaction on Nuclear Science, vol. 47, No. 4, Aug. 2000, pp. 1329-1336.

Meng, L.J. et al. "The design and performance of a large-volume spherical CsI (T1) scintillation counter for gamma-ray spectroscopy." *Nuclear Instruments and Methods in Physics Research*. A 485 (2002), pp. 468-476.

Meng, L.J. et al. "'Scintisphere'—The Shape of Things to Come in Gamma-Ray Spectroscopy." *IEEE Transactions on Nuclear Science*. Vol. 49, No. 4, Aug. 2002, pp. 1681-1686.

Berger, M.J. and S.M. Seltzer. "Response Functions for Sodium Iodide Scintillation Detectors." *Nuclear Instruments and Methods*. Vol. 104 (1972), pp. 317-332.

* cited by examiner

GAMMA-RAY CAMERA SYSTEM

This application is a national phase of International Application No. PCT/GB2004/000982 filed Mar. 9, 2004 and published in the English language.

BACKGROUND OF THE INVENTION

The invention relates to gamma-ray camera systems, in particular to spectral processing of data in gamma-ray camera systems.

Figure 1:
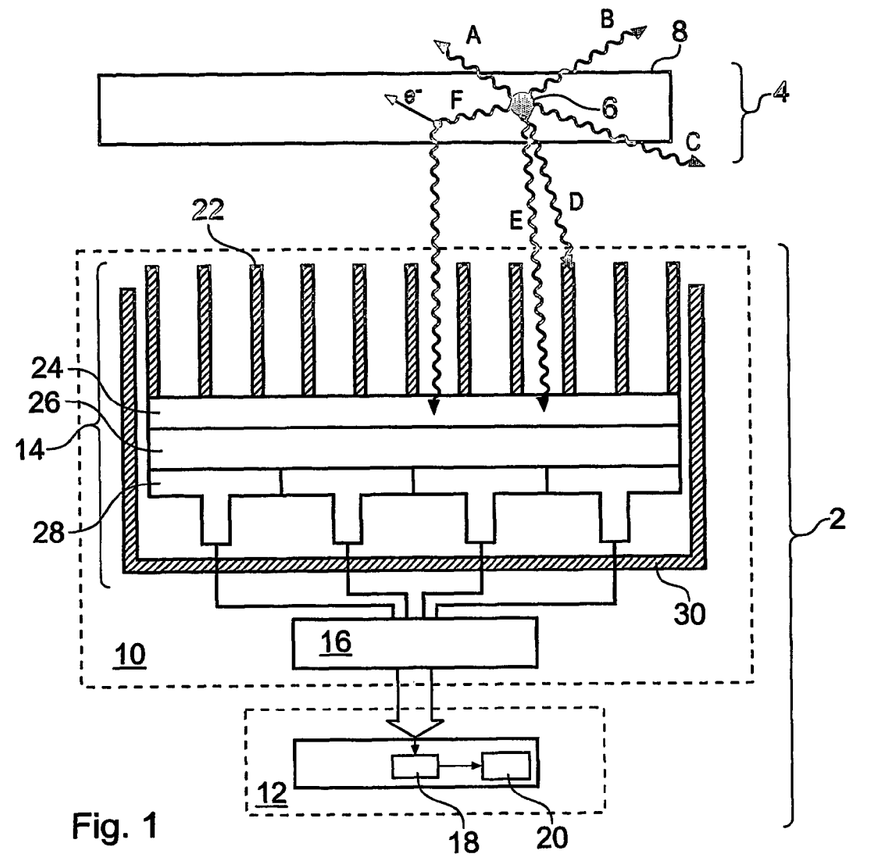
FIG. 1 schematically shows in vertical cross-section a prior art gamma-ray camera system viewing a sample containing a gamma-ray source.

FIG. 1 schematically shows in vertical cross-section a gamma-ray camera system 2 viewing a sample 4. In this case the sample comprises a point-like gamma-ray source 6 embedded within an extended body 8. The gamma-ray camera system comprises a gamma-ray camera 10 and an energy spectra accumulating component 12. The gamma-ray camera 10 is an Anger-type camera [1]. This is a type widely used as a diagnostic tool in nuclear medicine. The gamma-ray camera 10 includes a gamma-ray imager 14 coupled to a detector read-out component 16. The energy spectra accumulating component includes an energy spectra accumulator 18 and a data storage component 20.

The gamma-ray imager 14 includes a parallel collimator 22, a scintillator crystal 24, a light guide element 26 and a plurality of photo-multiplier tubes 28. The scintillator crystal is, for example, a large single crystal of Thallium doped Sodium Iodide (NaI(Tl)). The scintillator crystal is shielded from gamma-ray photons not incident through the parallel collimator by a shield 30.

The gamma-ray imager provides a 50 cm square image plane. The parallel collimator comprises an array of apertures with a characteristic cell size of 2 mm. Each cell provides a field-of-view of around 3°. The photo-multiplier tubes form a close packed hexagonal array of 61 tubes arranged to collectively view much of the 50 cm square scintillator crystal 24 forming the image plane.

During an exposure period, which in nuclear medicine imaging applications might typically be around 5 minutes, photons are emitted by the gamma-ray source in all directions. In a typical application, the photons will be emitted by radio-labelled pharmaceuticals in a patient's body (i.e. pharmaceuticals labelled with a radioactive tracer). In the example shown in FIG. 1, the gamma-ray source is Cobalt-57. Cobalt-57 primarily emits gamma-ray photons with an energy of around 122 keV. Six such photons, labelled A-F, are emitted in the plane of the figure as schematically shown in FIG. 1. Photons A, B and C exit the sample 4 in the directions indicated in the figure and are not seen by the gamma-ray camera. Photon D is emitted towards the gamma-ray camera, but is not sufficiently parallel to the axis of the parallel collimator 22 to pass through it. As can be seen from the figure, photon D is absorbed in a wall of the parallel collimator, and as such is not detected by the scintillator crystal 24. Photon E, however, does reach the scintillator crystal 24 since its path is within the parallel collimator's field-of-view. The energy of photon E is deposited in the scintillator crystal 24 in a scintillation event. A detection of this kind, where the gamma-ray photon travels directly between the gamma-ray source and the scintillator crystal, is known as a direct detection event. The detection event generates a pulse of optical radiation which illuminates several of the photo-multiplier tubes 28 via the light guide element 26. The light guide element assists in coupling the pulse of optical radiation from the scintillator crystal, which typically has a relatively high refractive index at visible wavelengths. In a typical scintillation event, the resulting pulse of optical radiation will be detected by up to seven of the photo-multiplier tubes.

The signals from the photo-multiplier tubes are supplied to the detector read-out component. The detector read-out component determines the X- and Y-coordinates of the scintillation event from the relative intensities of the signals seen by each of the photo-multiplier tubes. The detector read-out component also calculates the total energy deposited in the scintillation event from a summation of the signal amplitudes seen by the photo-multiplier tubes. Read-out components for Anger-type gamma-ray cameras are well known [1]. One mode of operation is known as list-mode operation. In this mode the detector read-out component outputs a signal in response to each scintillation event, the output signal including the calculated energy deposited in the scintillator crystal and the X- and Y-coordinates of the scintillation event. The output signals from the detector read-out component are coupled to the energy spectra accumulating component 12.

The functionality of the energy spectra accumulating component 12 in this example is provided by a suitably programmed general purpose computer. The computer includes an appropriate interface to receive and decode the output signals from the detector read-out component 16. The energy spectra accumulator 18 within the energy spectra accumulating component 12 operates to generate a three-dimensional observed data array I(X, Y, E). This array comprises a count of the number of scintillation events occurring within an exposure period as a function of their X, Y position within the detector, and the energy deposited in the scintillator crystal. A bin-size used in generating I(X, Y, E) is typically 5 mm for each spatial coordinates (i.e. X and Y) and 2 keV for the energy coordinate (i.e. E). Although the scintillator crystal 24 is a large single crystal, the 5 mm spatial binning used in generating I(X, Y, E) defines effective detector pixels, and these have a size of around 5 mm square. However, because of Compton scattering within the sample 4, the resolution in a resulting image is worse than this.

When an exposure is completed, the observed data array I(X, Y, E) is normalized to the exposure time and stored in the data storage component 20 of the energy spectra accumulating component for later analysis. I(X, Y, E) will typically be used in generating two-dimensional diagnostic images representing gamma-ray emission intensity from the source 4 as seen within selected gamma-ray energy ranges.

Figure 2:
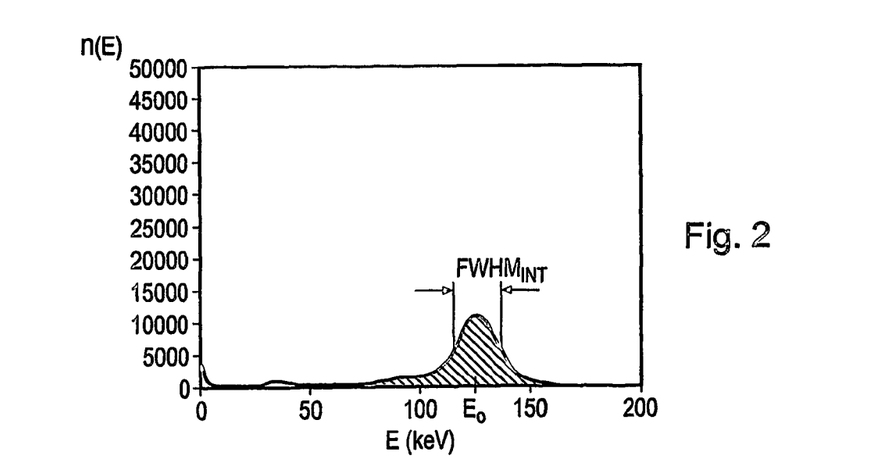
FIG. 2 schematically shows an example energy spectrum seen in one of the detector pixels of the gamma-ray camera system shown in FIG. 1 when viewing an isolated gamma-ray source.

FIG. 2 shows a typical energy spectrum which might be seen in one of the detector pixels of a gamma-ray camera system similar to that shown in FIG. 1. Count rate n(E) is plotted as a function of energy E for a detector pixel at position $X_0$, $Y_0$—i.e. $n(E)=I(X_0, Y_0, E)$. In this example, an isolated (i.e. not embedded in a body) gamma-ray point source is viewed to show the intrinsic energy resolution of the gamma-ray camera. The gamma-ray source is again Cobalt-57 emitting primarily at a photo-peak energy of $E_0=122$ keV. In FIG. 2 the full width at half maximum ($FWHM_{INT}$) of the peak corresponding to gamma-ray emission from the Cobalt-57 source is approximately 25 keV. Accordingly, at an energy of 122 keV the gamma-ray camera has an intrinsic energy resolution of around 20%. This relatively poor energy resolution is significantly worse than that predicted by photon-statistics alone and is due to several factors. One effect is the variance in the scintillation efficiency of the crystal itself, this is energy dependent and cannot be corrected for simply. Another effect is the non-uniformity of the response of the photo-multiplier tubes. This means scintillation events which deposit the same energy in the scintillator crystal will appear to have different energies depending on which photo-multiplier tubes are illuminated, and how the actual illumination falling on each individual photo-multiplier tube is distributed. A further effect is the variance in the light-collection efficiency of the scintillator crystal and photo-multiplier tube assembly for events which occur at different locations within the detector crystal.

When forming a diagnostic image from the stored data array I(X, Y, E), for example in order to represent the distribution of Cobalt-57 within the field-of-view of the gamma-ray camera, the relatively poor intrinsic resolution is not necessarily a significant problem with an isolated point-like gamma-ray source. This is because for each pixel in the image, the intensity of gamma-ray emission seen by the gamma-ray camera can be represented by a summation over the full width of the peak around 122 keV, for example between 100 keV and 150 keV. Because the poor energy resolution does not directly effect the imaging capabilities of the camera in such cases, a summation over this wide energy range provides the best signal-to-noise ratio possible by making use of all detected events, without unduly compromising image quality.

In practice, however, it will generally be necessary to generate diagnostic images of gamma-ray emission within the field-of-view of the gamma-ray camera by summing the energy spectra recorded in each pixel over a more restricted energy range than the full width of the peak seen in FIG. 2. This can be important, for example, to improve the signal-to-noise ratio in a derived diagnostic image, or to distinguish between different gamma-ray emission energies which can be used in some clinical observations. For example, in clinical studies Technetium-99 (which emits primarily at 140 keV) and Thallium-201 (which emits primarily at 80 keV) are sometimes used as radioactive tracers to examine the relative distribution of different pharmaceuticals in a patient. To differentiate spectrally between multiple gamma-ray sources in the field-of-view, it will not be possible to sum over all of the scintillation events relating to, say, the Thallium-201 emission without also including some of the scintillation events relating to the Technetium-99 emission due to the spectral overlap of the observed peaks. This means that it is not normally possible to make simultaneous observations of multiple radioactive tracers, and sequential observations must be made.

In cases where the field-of-view includes only a monochromatic source of gamma-ray emission, the poor energy resolution can still lead to degradation in derived diagnostic images where the source is embedded in a body. This is due to scattering, for instance Compton scattering, in the body surrounding the gamma-ray source.

The energy of gamma-rays emitted by radioactive sources used to label commonly-used pharmaceuticals in nuclear medicine is typically on the order of $10^2$ keV. For example, Technetium-99 emitting at 140 keV is commonly used. This energy is chosen to be sufficiently energetic to allow emitted gamma-ray photons to escape from the surrounding body in which the gamma-ray source is embedded, yet without being so energetic as to make collimation and detection difficult. One disadvantage of this choice of energy is that the gamma-ray photons have a relatively high probability of scattering within the surrounding body before being viewed by the gamma-ray camera. An example of such a scattering event is shown by the photon labelled F in FIG. 1.

Referring to FIG. 1, photon F is initially emitted by the gamma-ray source 6 in a direction away from the gamma-ray camera system 2. Photon F should not normally contribute to the observed data array I(X, Y, E). However, in the case shown in FIG. 1, photon F undergoes a Compton scattering event in the surrounding body 8 which scatters it towards the gamma-ray camera. The scattered photon passes through the parallel collimator 22 and is detected by the scintillator crystal 24. Photon F is scattered off an electron marked $e^-$ in FIG. 1. The electron carries away some of the energy of Photon F. As a result of the Compton scattering of photon F, the gamma-ray camera system records a scintillation event occurring at a position not commensurate with the position of gamma-ray photons arriving directly from the source 6, and at an energy slightly lower than of the gamma-ray photons arriving directly from the source 6. While for simplicity a point source of gamma-ray photons is shown in FIG. 1, in general there will be an extended gamma-ray source within the surrounding body. This means that not only are gamma-ray photons from an individual portion of an extended source mapped to a particular example pixel scattered into other pixels, but gamma-ray photons from other portions of the extended gamma-ray source are scattered into the example pixel. As a consequence, an additional source of background noise in introduced throughout the image. The additional background noise not only leads to a reduction in the sensitivity of the camera due to the reduced signal-to-noise ratio in each pixel, but also impacts on the spatial resolution of derived images as a Compton scattered halo becomes associated with each portion of the gamma-ray source due to the non-direct detection events. Non-direct detection events are known as Compton scattered detection events.

In order to minimise the deleterious effect of Compton scattering in the source, it is necessary to reject as many of the Compton scattered detection events as possible, without unnecessarily discarding too many of the direct detection events. As noted above, when a gamma-ray photon is Compton scattered, some of its energy is imparted to a free electron in the scattering material. This means that, in principle, it is possible to distinguish between direct detection events and Compton scattered detection events on the basis of the energy deposited in the scintillator material comprising the scintillator detector. However, the poor energy resolution of scintillator crystal based gamma-ray camera systems is not able to provide suitable energy discrimination at 140 keV to make this an efficient process.

Figure 3:
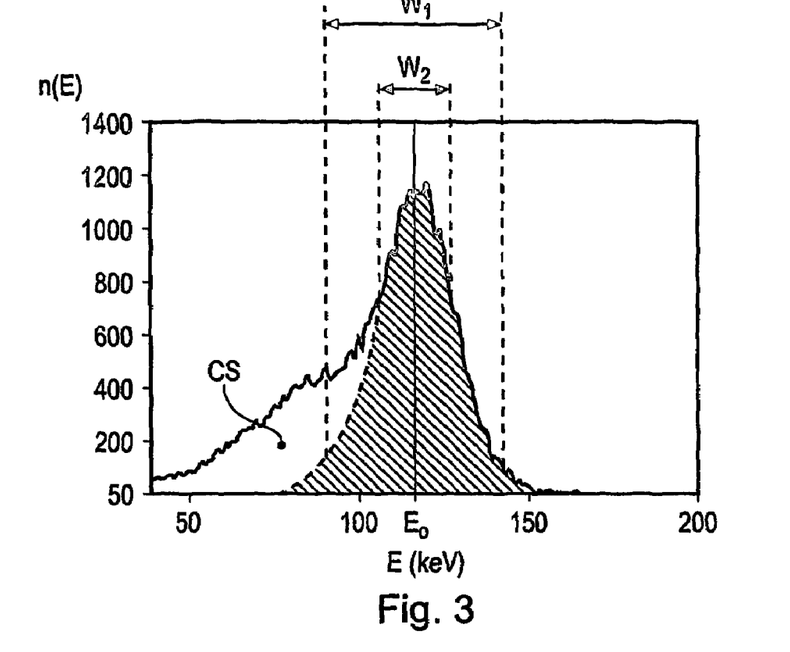
FIG. 3 schematically shows an example energy spectrum seen in one of the detector pixels of the gamma-ray camera system shown in FIG. 1 when viewing a gamma-ray source surrounded by a body in which Compton scattering occurs.

FIG. 3 shows a typical energy spectrum which would be seen in one of the detector pixels of a gamma-ray camera system similar to that shown in FIG. 1. As with FIG. 2, count rate n(E) is plotted as a function of energy E for a single pixel at position $X_0$, $Y_0$—i.e. $n(E)=I(X_0, Y_0, E)$. The gamma-ray source is again Cobalt-57 emitting primarily at an energy of $E_0$=122 keV. However, in the example shown in FIG. 3, data is obtained with the gamma-ray source positioned behind a 5 cm thick body of water, as opposed to in isolation. The body of water corresponds to the surrounding body 8 shown in FIG. 1, and it is in this body of water that Compton scattering can occur leading to Compton scattered detection events being detected.

On the high energy side of the peak seen in FIG. 3 the detected count rate profile is generally similar to that seen in FIG. 2. However, on the low energy side there is a significant increase in count rate compared to the same region of the spectrum shown in FIG. 2. The excess count rate in this region of the spectrum is due to Compton scattered detection events. In order to highlight the magnitude of the contribution of these events, an estimate of the profile which would be seen in the absence of Compton scattering is marked with a dashed line in FIG. 3. The corresponding area under the curve shown in FIG. 3 estimated to derive from only direct detection events is identified by hatching. The un-hatched area under the curve, which is marked CS, reflects the contribution to the count rate due to Compton scattered detection events. In generating a diagnostic image to represent the distribution of Cobalt-57 in the field-of-view from data such as shown in FIG. 3, it is necessary to determine an appropriate energy-width, known as an energy window, over which to sum the count rate n(E). The energy window must be chosen to obtain a summed count rate reflecting as many direct detection events as possible, while rejecting as much of the contribution from Compton scattered detection events as possible. Determining the most appropriate width of energy window will generally be a matter of compromise. For example, if an energy window such as that marked $W_1$ in FIG. 3 were to be used, most of the direct detection events would be included in the image generation as desired. However, with this wide energy window a significant fraction of Compton scattered detection events will also be included. If, on the other hand, a narrower energy window were to be employed, such as the one marked $W_2$ in FIG. 3, there would be a significant reduction in the number of Compton scattered detection events included in the summation, both in absolute and relative terms. However, with a narrower energy window there would also be a reduction in the number of direct detection events included. This leads to derived diagnostic images with a poor signal-to-noise ratio.

Figure 4A:
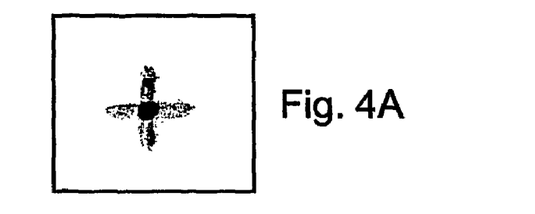
FIG. 4A schematically shows an example diagnostic image of a gamma-ray source which would be obtained with an idealized gamma-ray camera system.

FIG. 4A schematically shows in negative an idealized diagnostic image of an example extended gamma-ray source distribution obtained using an idealized gamma-ray camera system. The example source distribution is in the form of a cross with a bright spot at the centre, and the source distribution is directly reflected in the resulting image.

Figure 4B:
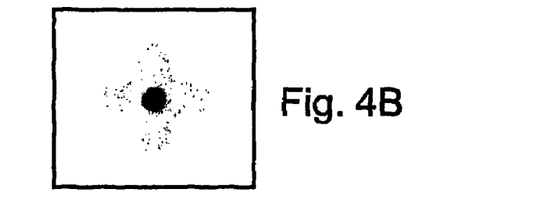
FIG. 4B schematically shows an example diagnostic image of the same gamma-ray source obtained using the gamma-ray camera system shown in FIG. 1 formed using a broad energy window.
Figure 4C:
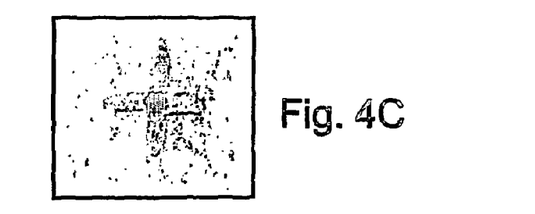
FIG. 4C schematically shows an example diagnostic image of the same gamma-ray source obtained using the gamma-ray camera system shown in FIG. 1 formed using a narrow energy window.

FIGS. 4B and 4C schematically show how the same example gamma-ray source distribution imaged in FIG. 4A would appear when imaged with a gamma-ray camera system of the kind discussed and using different width energy windows.

FIG. 4B shows the result of using a wide energy window, such as the one marked $W_1$ in FIG. 3. As outlined above, the inclusion of a significant fraction of Compton scattered detection events leads to relatively poor spatial resolution in the generated image due to the Compton scattered halo appearing to surround each element of the gamma-ray source. FIG. 4C shows the result of using a narrow energy window such as the one marked $W_2$ in FIG. 3. As outlined above, the rejection of a significant fraction of non-Compton scattered events leads to a reduction in the appearance of the Compton scattered halo, but with a correspondingly reduced signal-to-noise ratio. This causes the image to appear faint against a relatively high background noise level.

As a consequence of the failings of gamma-ray camera systems of the type described above, alternative designs for gamma-ray camera systems which help to improve the rejection of Compton scattered detection events while maintaining the direct detection events have evolved.

For example, a number of research groups are seeking to exploit the improved energy resolution characteristics of room-temperature semiconductor detectors such as CdZnTe. These are capable of providing an intrinsic full width at half maximum energy resolution of around 4% at 140 keV [2]. This compares favourably with the approximately 20% seen above for an Anger-type gamma-ray camera system. The improved energy resolution allows a narrower energy window to be employed whilst retaining many more of the direct detection events since these are now contained in a narrower spectral peak. However, there are a number of disadvantages associated with this type of design. For example, each detector pixel requires a separate read-out electronics channel, the detection efficiency is relatively low and the camera costs are high.

Improved energy resolution has also been achieved in the recently introduced "2020tc Imager" camera manufactured by Digirad, San Diego, USA. This uses silicon positive-intrinsic-negative (PIN) diodes to record the scintillation flash generated in a large array of discrete Caesium Iodide (CsI) scintillation crystal elements. However, this design again requires significantly increased complexity in the read out electronics in comparison to other types of gamma-ray camera system, such as the kind discussed above.

Methods of improving the spectral resolution of non-imaging scintillator-based gamma-ray detectors by post-exposure spectral processing have also been described [3, 4, 5]. These techniques involve determining a detector response function for the single element detector and deconvolving this response function from observed spectra. However, these techniques have been applied only to single element specific scintillator geometries so as to provide a calculable transfer function describing the response of a photo-detector to pulses of optical photons from a scintillation event.

Various other schemes for reducing the effect of Compton scattered detection events in gamma-ray camera systems have been attempted.

U.S. Pat. No. 5,903,008 describes the use of dual energy-windows for diagnostic image formation [6]. This dual energy-window technique measures the relative number of counts recorded in two energy channels; one centred on the photo-peak energy and the second, some 10-15% below that energy. This ratio is measured initially when there is no scattering present. Thereafter, the photo-peak values are modified according to the value of the number of counts in the lower window. This value is dominated by the presence of scattered events.

U.S. Pat. No. 5,530,248 describes a scheme for theoretical modelling of the contribution of Compton scattered detection events to the energy spectra [7]. This technique generates a trial function from the energy spectrum recorded in each pixel when no scattering material is present. This is achieved by taking the first differential of the spectrum to emphasise the photo-peak. This modified function is then fitted to the energy spectra seen when a scattering medium is present in order to distinguish between 'wanted' and 'unwanted' photons.

U.S. Pat. No. 5,633,499 describes a scheme based on calculating a correction table to be applied to an image acquired using a conventional method of selecting only those events that fall within an energy window spanning ±10% of the photo-peak [8]. The correction value is derived from the measurement of the centroid of the spectrum recorded in a particular detector pixel. The data are used to estimate the scatter contribution.

U.S. Pat. No. 5,561,297 describes a spectrum subtraction method [9]. This method in essence uses the idea of subtracting a reference spectrum for each detector pixel form an observed spectrum. The subtracted reference spectrum is that recorded in the absence of a scatterer.

SUMMARY OF THE INVENTION

According to a first aspect of the invention there is provided a gamma-ray camera system comprising: a gamma-ray imager including detector pixels formed from a scintillator material; a detector read-out component for determining positions and energies of scintillation events occurring within the scintillator material; an energy spectra accumulating component for compiling observed energy spectra of scintillation events in the detector pixels; and a spectra processing component operable to deconvolve a pixel specific detector response function from the observed energy spectra.

By deconvolving detector response functions which are dependent on individual detector pixels from the observed energy spectra, much higher energy resolution can be obtained when compared to previously described systems. The higher energy resolution allows, for example, improved images to be formed where there is significant Compton scattering in a source being imaged. The higher energy resolution also allows radioactive sources emitting gamma-ray photons at different, though similar, energies to be better distinguished. Whereas with previous systems, it has generally been necessary to make sequential observations of a subject in order to study how different pharmaceuticals marked with different radioactive tracers are taken up in a body, improved energy resolution allows different radioactive tracers to be simultaneously imaged and separated in a single observation.

In one example, the detector response functions are selected from a store of detector response functions which include detector response functions specific to individual detector pixels.

By providing a separate detector response function for each individual detector pixel, the most accurate mapping of the detector response to detector pixel can be obtained.

Alternatively, the detector response functions may be selected from a store of detector response functions which comprises a family, and for the pixels in the gamma-ray image a detector response function is selected from the family.

By providing a number of detector response functions which is fewer than the number of detector pixels, a compromise can be made between the benefits of providing individual detector response functions for each detector pixel, and the benefits of working with a reduced number of detector response functions, for instance reduced storage requirements.

The invention is equally applicable to a range of gamma-ray camera systems employing different detection planes. For instance, an Anger-type gamma-ray imager in which the scintillator material comprises a single scintillator crystal optically coupled to a plurality of photo-detectors may be used. Alternatively, other types of gamma-ray imager may be employed, for example, gamma-ray imagers in which the scintillator material comprises an array of discrete scintillator crystal elements optically coupled to a corresponding array of discrete photo-detectors.

According to a second aspect of the invention there is provided a method of processing energy spectra recorded in detector pixels of a gamma-ray scintillation camera comprising: providing observed energy spectra recorded in the detector pixels; and deconvolving a pixel specific detector response function from the observed energy spectra.

This method provides much higher energy resolution than previous methods of processing data from gamma-ray camera systems and correspondingly provides similar benefits to those of the first aspect of the invention described above.

The method of processing energy spectra may include selecting detector response functions from a store of detector response functions which include a detector response function specific to individual detector pixels.

Alternatively, the method may include selecting detector response functions from a store of detector response functions which comprises a family, and for the detector pixels a detector response function is selected from the family.

A computer program product bearing machine readable instructions for implementing the method is also provided.

According to a third aspect of the invention there is provided a method of generating pixel-specific detector response functions for a gamma-ray imager including detector pixels formed from a scintillator material comprising: obtaining a theoretical component to the detector response as a function of position by performing a simulation; obtaining an empirical component to the detector response as a function of position by observing the response of the gamma-ray imager to a calibration source; and combining the theoretical and empirical components to provide detector response functions for the detector pixels.

A computer program product bearing machine readable instructions for implementing the method and a data storage medium bearing detector response functions calculated according to the method are also provided.

BRIEF DESCRIPTION OF THE DRAWINGS

For a better understanding of the invention and to show how the same may be carried into effect reference is now made by way of example to the accompanying drawings in which.

DETAILED DESCRIPTION

Figure 5:
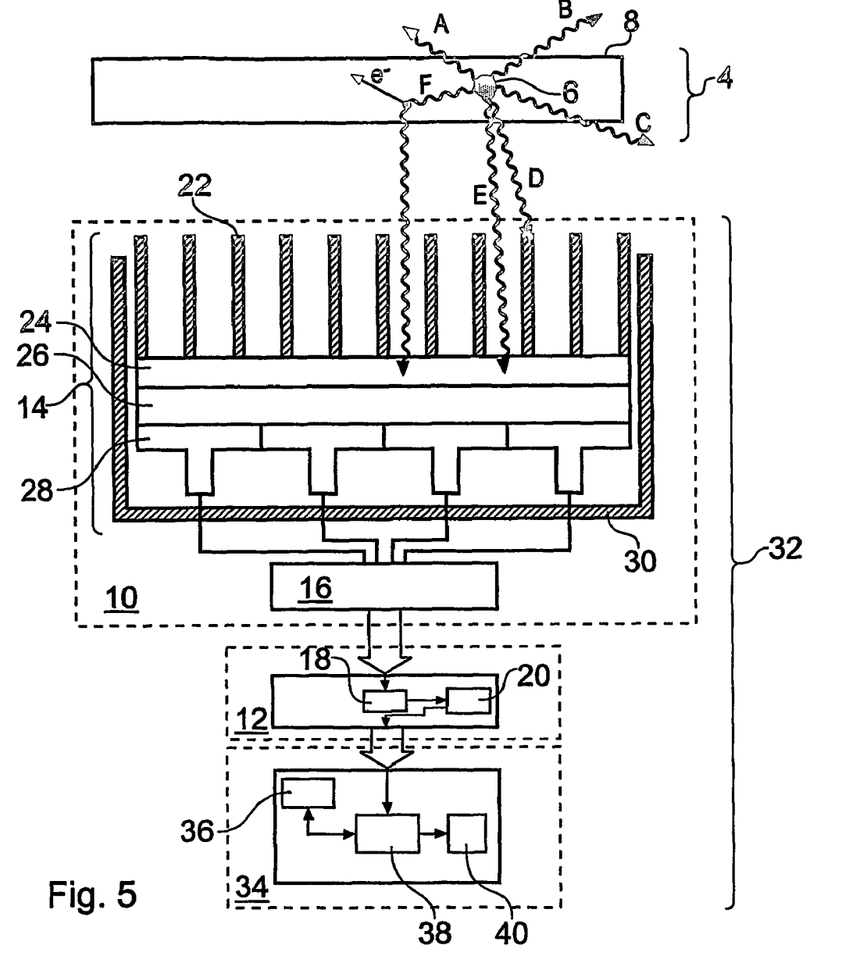
FIG. 5 schematically shows in vertical cross-section a gamma-ray camera system according to a first embodiment of the invention viewing a sample containing a gamma-ray source.

FIG. 5 schematically shows in vertical cross-section a gamma-ray camera system 32 according to a first embodiment of the invention. Many of the features of the gamma-ray camera system 32 shown in FIG. 5 are similar to and will be understood from the correspondingly numbered features shown in FIG. 1 and described above. However, the gamma-ray camera system 32 additionally includes a spectra processing component 34. The spectra processing component includes a store of detector response functions 36, a spectra processor 38 and a data storage component 40. The functionality of the spectra processing component in this example is provided by a suitably configured general purpose computer. However, an application specific integrated circuit (ASIC), a field programmable gate array (FGPA) or a digital signal processor (DSP) may also be employed.

The spectra processing component 34 is arranged to read the observed data array I(X, Y, E) from the data storage component 20 in the energy spectra accumulating component 12. When an exposure is completed and an observed data array I(X, Y, E) generated as described above, the observed data array is read by the spectra processor 38 in the spectra processing component 34. The spectra processor is operable to deconvolve a detector response function from the individual spectra associated with each pixel in the observed data array I(X, Y, E), the specific detector response function employed in the deconvolution is selected from a store of detector response functions 36. The choice of detector response function is based on which detector pixel the spectrum currently being processed is associated with. Once each of the energy spectra comprising the observed data array I(X, Y, E) have been deconvolved, the resulting refined energy spectra are collated into a refined data array S(X, Y, E). The refined data array is of the same form as I(X, Y, E) and may be used in the same way to generate diagnostic images.

With a gamma-ray camera system of the type shown in FIG. 5, the energy spectrum n(E) formed by the spectra accumulating component 12 for a detector pixel at position $X_0, Y_0$ in response to an incident gamma-ray spectrum A(E) is given by:

$$n(E) = \int_0^\infty (R_{X_0 Y_0}(E, E') \cdot A(E') + \varepsilon(E)) \cdot dE'$$

where $R_{X_0 Y_0}(E, E')$ describes the detector response function for the detector pixel at position $X_0, Y_0$ and $\varepsilon(E)$ is the noise contribution. This integral can be discretised as:

$$\begin{bmatrix} n_1 \\ n_2 \\ . \\ . \\ . \\ n_l \end{bmatrix} = \begin{bmatrix} R_{X_0 Y_0}^{11} & R_{X_0 Y_0}^{12} & \cdots & R_{X_0 Y_0}^{1m} \\ R_{X_0 Y_0}^{21} & R_{X_0 Y_0}^{22} & \cdots & R_{X_0 Y_0}^{2m} \\ . & . & . & . \\ . & . & . & . \\ . & . & . & . \\ R_{X_0 Y_0}^{l1} & R_{X_0 Y_0}^{l2} & \cdots & R_{X_0 Y_0}^{lm} \end{bmatrix} \cdot \begin{bmatrix} A_1 \\ A_2 \\ . \\ . \\ . \\ A_l \end{bmatrix} + \begin{bmatrix} \varepsilon_1 \\ \varepsilon_2 \\ . \\ . \\ . \\ \varepsilon_l \end{bmatrix}$$

where the detector response function is parametrized such that $R_{X_0 Y_0}^{lm}$ describes the probability that a detected gamma-ray photon which generates a scintillation event in pixel $X_0$, $Y_0$, and having an incident energy falling into energy bin l, will be actually detected as having an energy falling within bin m. A thorough description of techniques which can be used to deconvolve $R_{X_0 Y_0}^{lm}$ from $n_{l \ldots l}$ to determine the incident gamma-ray spectrum $A_{l \ldots l}$ is given by Berger & Seltzer [10].

Figure 6:
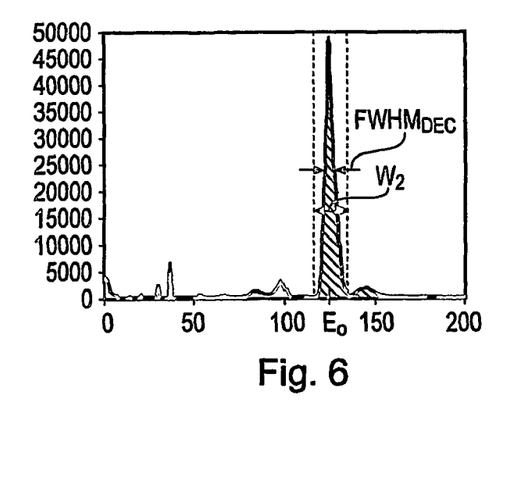
FIG. 6 schematically shows an example energy spectrum which might be seen in one of the detector pixels of the gamma-ray camera system shown in FIG. 5 when viewing an isolated gamma-ray source.

FIG. 6 shows a typical energy spectrum which would be seen in one of the detector pixels of a gamma-ray camera system similar to that shown in FIG. 5. In this example, as with the example shown in FIG. 2, an isolated (i.e. not embedded in the body) gamma-ray point source is viewed to show the intrinsic energy resolution of a gamma-ray camera system including deconvolution. This allows the performance of the gamma-ray camera system shown in FIG. 5 to be directly compared with that shown in FIG. 1. As with the data shown in FIG. 2, the gamma-ray source is Cobalt-57 emitting primarily at an energy $E_0$=122 keV. As with FIG. 2, count rate n(E) is plotted as a function of energy E for a detector pixel at position $X_0, Y_0$. In this case, however, $n(E)=S(X_0, Y_0, E)$, i.e. it is a deconvolved energy spectrum which is plotted and not the observed energy spectrum. The detector response function employed in the deconvolution is determined as detailed further below. In FIG. 6 the deconvolved full width at half maximum ($FWHM_{DEC}$) of the peak corresponding to gamma-ray emission from the Cobalt-57 source is approximately 6 keV. Accordingly, at an energy of 122 keV the gamma-ray camera system shown in FIG. 5 has an energy resolution of around 5%. This is a significant improvement on the energy resolution of around 20% seen with previous gamma-ray camera systems such as shown in FIG. 1.

The much improved resolution makes it easier to distinguish Compton scattered detection events from direct detection events when forming diagnostic images from the refined data array S(X, Y, E). This is possible since a narrower energy widow around the peak energy may be used when generating diagnostic images so as to discard much of the Compton scattered detection events, while maintaining most of the direct detection events. For instance, the width of the narrow energy window $W_2$ shown in FIG. 3 is also marked on FIG. 6. While in FIG. 3 this window excluded a significant fraction of the direct detection events, it can be seen from FIG. 6 that after appropriate deconvolution, most of the direct detection events are included within the window. The broad energy distribution of the Compton scattered detection events is inherent in their contribution to the incident gamma-ray spectrum A(E). This means that the deconvolution does not significantly affect the spectral distribution of the Compton scattered detection events and they remain largely outside of the narrower energy window $W_2$, as seen in FIG. 3.

The difficulties in applying this technique to gamma-ray camera systems are the complications introduced by the fact that the response of a relatively large single scintillator crystal is not only a function of photon energy, but it is also a function of the location of the gamma-ray interaction. This means that it is necessary to construct a model of the detector response function not only for the way that gamma-rays interact in the scintillator crystal material itself, but it is also necessary to modify this model with reference to an empirical calibration of the overall response of the gamma-ray camera system on a detector pixel by detector pixel basis. The detector response function varies from one detector pixel to another as a consequence of non-uniformities in the scintillator crystal light-yield, and also in the light-collection efficiency on the gamma-ray camera imager. For example, the light collection efficiency will depend on detector pixel both due to differences in transfer function from different scintillation sites to the photo-multiplier tubes, and also to non-uniformities in the response of the photo-multiplier tubes. Further variations in the detector response function for different detector pixels are introduced as a consequence of non-linearities in the response of the scintillation crystal as a function of energy deposited in a scintillation event.

By using, for example, a Monte Carlo technique, it is possible to predict the way that the scintillator material responds to incident gamma-ray photons at energies within an energy range of interest, for instance between 50 keV and 500 keV. Other modelling methods could also be used. This information may then be combined with empirical calibration data to provide information on how the gamma-ray imager actually responds at a number of discrete energies within the same region of interest. The calibration data may be acquired, for example, by observing a number of monochromatic radio-active sources emitting within the energy range of interest. By experimentally determining the response of each individual detector pixel to known incident gamma-ray energy spectra, the positional dependence of the detector is response function can be determined. With a point calibration source, data can be obtained for each pixel simply by removing the collimator and placing the source at a distance of say 50 cm from the scintillator crystal, or by mounting the calibration source on a translation stage such that it can be scanned across the field-of-view of the camera. It is most appropriate to determine how the detector response function varies with position at a spatial resolution comparable with that of the gamma-ray imager. The determined detector response functions are specific to an individual gamma-ray camera.

It will also be appreciated that while in the above examples a Monte Carlo or similar simulation provides a base model which is modified according to empirically determined calibration data, in other examples the simulation may be dispensed with. In such cases purely empirical pixel specific detector response functions can be obtained from observations of the response of the gamma-ray imager to point calibration source.

With accurate models for the way in which the gamma-ray imager responds as a function of incident gamma-ray photon energy, deconvolution can be performed on a detector pixel by detector pixel basis using the techniques noted above [10]. Accordingly, following an exposure, when energy spectra for each detector pixel have been recorded in an observed data array I(X, Y, E) as described above, the gamma-ray spectrum incident on each detector pixel can be recovered using the position-sensitive detector response functions in a standard deconvolution algorithm.

Figure 7:
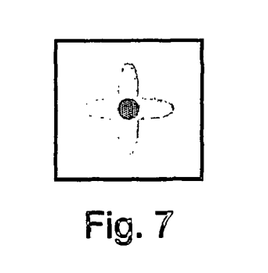
FIG. 7 schematically shows an example diagnostic image of the same gamma-ray source as imaged in FIGS. 4A-C obtained using the gamma-ray camera system shown in FIG. 5 and formed using a narrow energy window.

FIG. 7 schematically show how the same gamma-ray source leading to the idealized image shown in FIG. 4A would appear when obtained with a gamma-ray camera system shown in FIG. 5. In this example, the energy window shown in FIG. 6 and marked $W_2$ is used in generating the diagnostic image. Since the narrow energy window excludes a high fraction of the Compton scattered detection events, there is no Compton scattered halo surrounding the image as seen with a wide energy window, for example as shown in FIG. 4B. The improved spectral resolution provided by the spectra processing component also ensures that the narrow energy window includes almost all of the direct detection events. This leads to a higher signal-to-noise ratio than that seen in the image shown in FIG. 4C. Accordingly, the gamma-ray camera system shown in FIG. 5 is able to provide diagnostic images which are much more closely matched to the idealized image shown in FIG. 4A than prior art gamma-ray camera systems.

Figure 8:
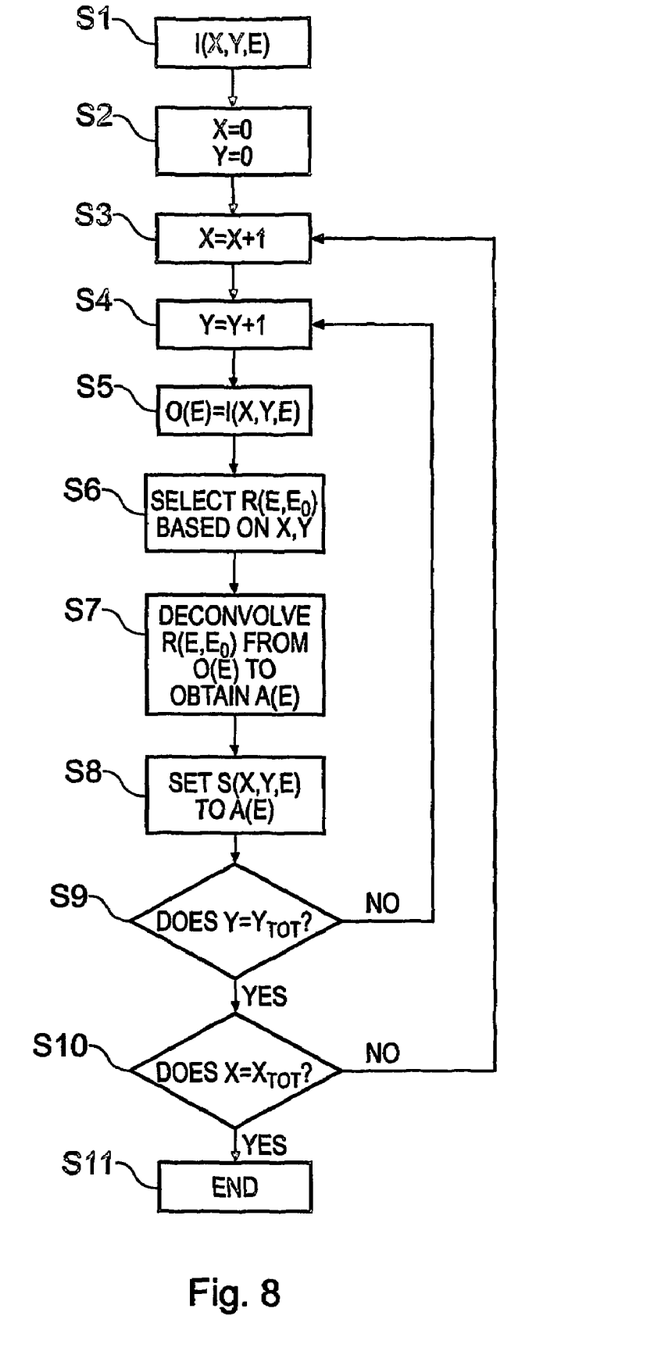
FIG. 8 shows a flow chart which schematically details some of the operational steps performed within a spectra processing component in the gamma-ray camera system shown in FIG. 5.

FIG. 8 is a flow chart which schematically details some of the operational steps performed within the spectra processing component 34. In this example, the gamma-ray camera imager provides a square array of $X_{TOT}$ by $Y_{TOT}$ detector pixels. At S1, an observed data array I(X, Y, E) obtained during an observation of interest is read from the data storage element 20 shown in FIG. 5. In S2, iteration parameters X and Y are set to zero. At S3 and S4, the iteration parameters X and Y are respectively incremented by one. In S5, the spectrum corresponding to the detector pixel X, Y is copied into a one-dimensional data array O(E). In S6, a detector response function R(E, $E_0$) is retrieved from the detector response function store 36. As noted above, the selected detector response function is selected based on the values of X and Y. In S7, the selected detector response function is deconvolved from O(E) to provide a one dimensional data array A(E). A(E) accordingly represents a calculation of the incident gamma-ray spectrum falling on detector pixel X, Y. In S8, the array A(E) is copied to the elements of a refined data array S(X, Y, E) which correspond to the detector pixel currently being processed. In S9, the value of Y is tested to determine whether it is equal to $Y_{TOT}$. If Y is less than $Y_{TOT}$, the process flow returns to S4. Steps S4-S8 are repeated, with Y being incremented at S4 in each iteration, until Y is equal to $Y_{TOT}$. In S10, the value of X is tested to determine whether it is equal to $X_{TOT}$. If X is less than $X_{TOT}$, the process flow returns to S3. Steps S3-S9 are repeated, with X being incremented at S3 in each iteration, until X is equal to $X_{TOT}$. In S11, the spectra processing is completed and the refined data array S(X, Y, E) is written to the data storage component 40. S(X, Y, E) is then available for further use from the data storage component in the spectra processing component in the same way that the observed data array I(X, Y, E) is available in prior art gamma-ray camera systems.

Because there are more than 2000 detector pixels present in the gamma-ray camera system, the process shown in FIG. 8 can be very time consuming. If faster processing is required, a fast parallel-processor may be used to accelerate the process such that diagnostic images can be made available within a time period which is comparable with the exposure time required to acquire the observed data array. Again, the functionality of the processing component 34 can be achieved by using a suitably configured general purpose computer with parallel processing capability, or an application specific integrated circuit.

Figure 9:
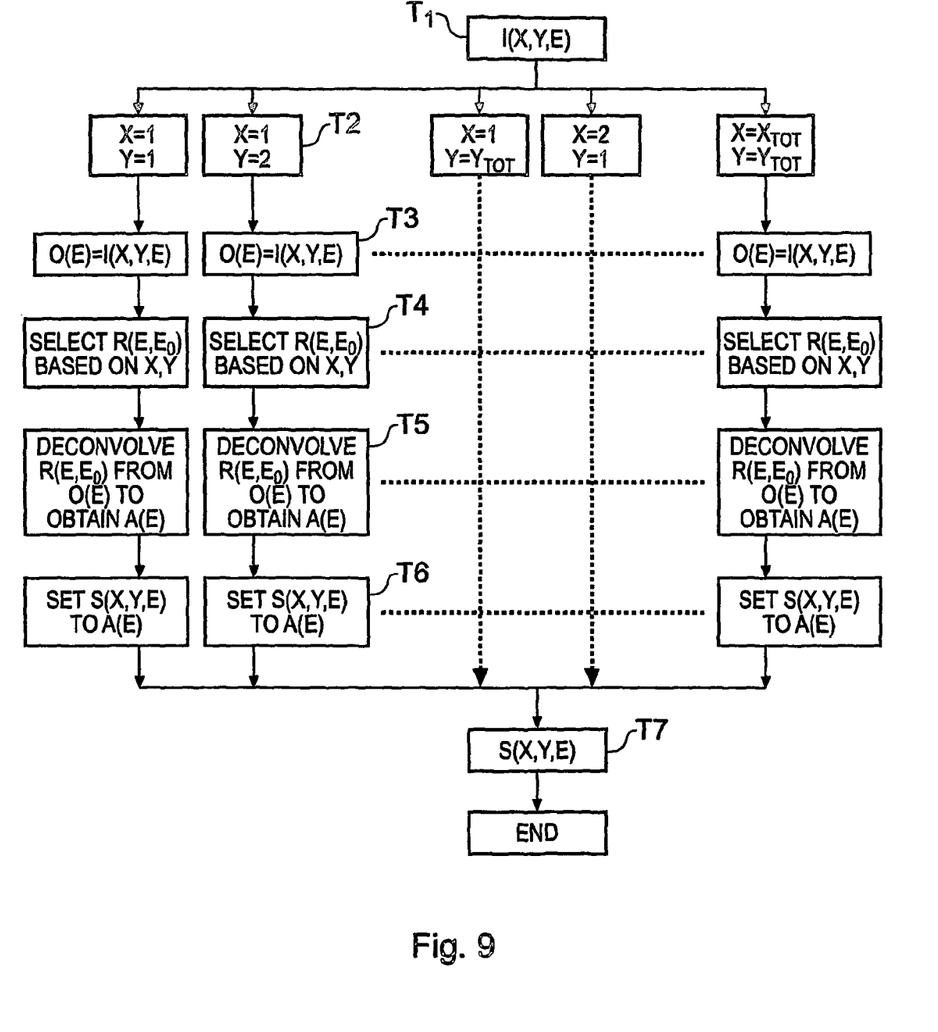
FIG. 9 shows a flow chart which schematically details some of the operational steps performed within a spectra processing component in a gamma-ray camera system according to a second embodiment of the invention.

FIG. 9 is a flow chart which schematically details some of the operational steps performed within a spectra processing component employed in a gamma-ray camera system according to second embodiment of the invention. As above, the gamma-ray camera imager provides a square array of $X_{TOT}$ by $Y_{TOT}$ detector pixels. At T1, the observed data array I(X, Y, E) corresponding to a prior observation is read from the data storage element 20 shown in FIG. 5. In this embodiment, the spectra processing component is configured to process the spectra associated with each detector pixel in parallel. A separate process thread operates for each individual detector pixel, this removes the need to iterate seen FIG. 8, and provides for significantly faster processing. In the first step of one process thread, labelled T2 in FIG. 9, the detector pixel corresponding to X=1 and Y=2 is selected. At the same time, threads corresponding to all other detector pixels are similarly instigated. In T3, the next step in the thread started at T2, the spectrum corresponding to the detector pixel X=1, Y=2 is copied into a one-dimensional data array O(E). In T4, a detector response function R(E, $E_0$) is retrieved from a detector response function store similar to that described above for the gamma-ray camera system shown in FIG. 5. The selected detector response function is chosen based on the values of X and Y corresponding to the thread being processed, in this case, 1 and 2 respectively. In T5, the detector response function is deconvolved from O(E) to provide a one dimensional data array A(E). A(E) accordingly represents a calculation of the incident gamma-ray spectrum falling on detector pixel X=1, Y-2. In T6, the array A(E) is copied to the elements of a refined data array S(X, Y, E) which correspond to the detector pixel X=0, Y=2. In T7, each process thread is finished, and a completed refined data array S(X, Y, E) is obtained. In T8, the spectra processing is complete and the refined data array S(X, Y, E) is written to a data storage component similar to the one described above for the gamma-ray camera system shown in FIG. 5. S(X, Y, E) is then available for further use in the same way that the observed data array I(X, Y, E) is made available in prior art gamma-ray camera systems.

In other examples, a combination of the methods shown in FIGS. 8 and 9 is could be employed. For example, an observed data array I(X, Y, E) including energy spectra for a total of 2000 pixels might be processed using twenty parallel processor channels, with each process channel sequentially processing 100 energy spectra. This would allow, for example, faster processing of the observed data array than would be seen using the method shown in FIG. 8, but would not require the same level of computing power necessary for the method shown in FIG. 9.

Whilst in the above examples, individual detector response functions are determined and stored for each detector pixel, it will be appreciated that in some circumstances the variation of detector response on spatial scales comparable to the detector pixel size will be small. In such cases, it may be unnecessary to store a detector response function for each pixel. For instance, in a gamma-ray camera system with a 50 cm square scintillator crystal detector and an imaging resolution of 5 mm, detector response functions may be determined with a spatial resolution of, for example, 1 cm. In this way a family of detector response functions are calculated corresponding to an array of 1 cm square elements spanning the scintillator crystal. When selecting a suitable detector response function to deconvolve form the observed data array corresponding to detector pixel at X, Y, the detector response function corresponding to the 1 cm square element which includes detector pixel X, Y is chosen.

While the above described examples of gamma-ray camera systems have used Anger-type gamma-ray cameras, it will be appreciated that in other embodiments spectra processing components of the type described above may be used in conjunction with other gamma-ray camera types.

Figure 10:
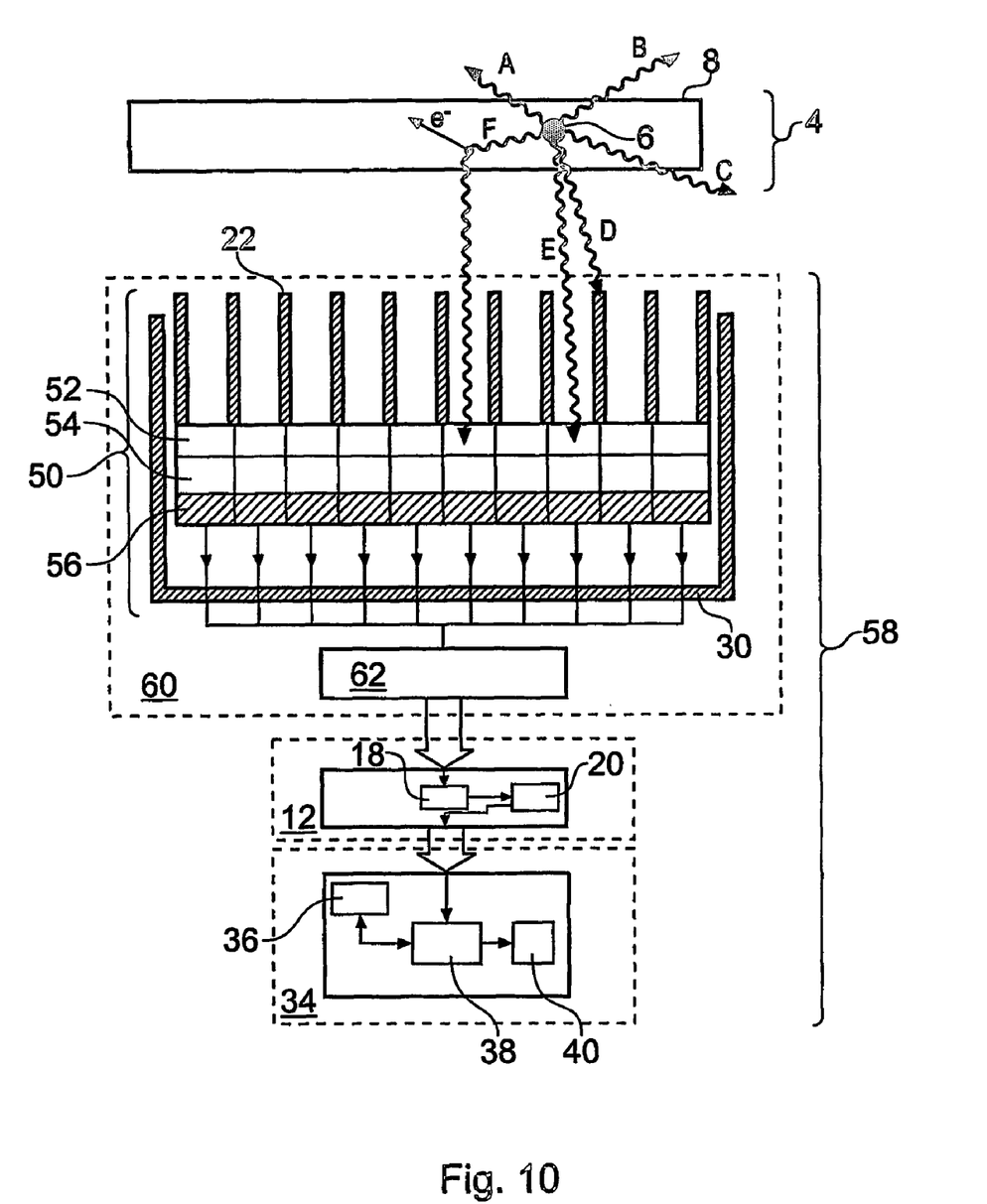
FIG. 10 schematically shows in vertical cross-section a gamma-ray camera system according to a third embodiment of the invention.

FIG. 10 schematically shows in vertical cross-section a gamma-ray camera system 58 according to a further embodiment of the invention. Many of the features of the gamma-ray camera system 58 shown in FIG. 10 are similar to and will be understood from the correspondingly numbered features shown in FIG. 5 and described above. However, in the example shown in FIG. 10 a modified gamma-ray camera 60 is used. In this example, a discrete detector element gamma-ray camera imager 50 replaces the gamma-ray camera imager 14 shown in FIG. 5. In place of the single scintillator crystal 24, light guide element 26 and family of photo-multiplier tubes 28 seen in FIG. 5, a detection plane comprising discrete scintillator crystal elements 52 coupled by discrete light guide elements 54 to individual photo-detectors 56 are used. This is type of gamma-ray imager is similar to the Digirad "2020tc Imager" camera discussed above. The photo-detector signals are coupled to a read-out component 62 which is configured to provide a list mode output to the spectra accumulating component 12 similar to that described above. The spectra accumulating component 12 and spectra processing component 34 function as described above.

As noted above, the detector response functions associated with the different detector pixels in a gamma-ray camera system are specific to each particular gamma-ray camera system. Accordingly, appropriately calculated detector response functions may be provided along with a gamma-ray camera system at first supply to an end user. In cases where the functionality of the spectra processing component is to be provided by a general purpose computer, the calculated detector response functions and software operable to configure the general purpose computer may be supplied together or separately on a computer program product, for instance a CD-ROM or other data-storage medium. In cases where the functionality of the spectra processing component is to be provided in firmware or hardware, for example by an ASIC, a FPGA or a DSP, the calculated detector response functions can, for example, be stored in ROM on an integrated chip along with the firmware.

In addition to being shipped together at first supply, spectra processing components similar to those described above can be coupled to existing gamma-ray camera systems as an 'after-market' add-on for improving energy resolution. To provide the best possible improvements in energy resolution, an existing user of a gamma-ray camera system may provide a third party with access to the camera system, such that the third party can fully calculate the detector response functions using the techniques described above. Alternatively, the existing user might supply the third party with appropriate calibration data from the gamma-ray camera from which the third party calculates the appropriate detector response functions to be supplied to the existing user. As above, the detector response functions may be supplied alone, for example on a data-storage medium, or along with a computer program product bearing machine readable instructions for implementing the functionality of a spectra processing component. In other cases, a hardware add-on may be supplied to an existing user. The hardware add-on including, for example, an appropriately configured interface for interfacing with the detector read-out component of the existing gamma-ray camera system, firmware or hardware, for example an ASIC, a FPGA or a DSP, for providing the functionality of a spectra processing component, and a memory, for example ROM or a replaceable data-storage medium, for storing appropriate detector response functions.

While in the above examples, the detector response functions are calculated for individual gamma-ray camera systems, improvements in spectral resolution may also be achieved by deconvolving more generic pixel dependent detector response functions. For example, for commonly used configurations of gamma-ray camera system, detector response functions may be calculated for each detector pixel in a manner dependent only on properties of the scintillator material and the geometric configuration of the gamma-ray camera imager.

This could be done, for example, by performing a Monte Carlo modelling simulation of a commonly used gamma-ray camera imager configuration without subsequently modifying the model according to specific calibration data obtained with an individual example gamma-ray camera imager. By disregarding effects which are specific to individual gamma-ray camera imagers, for example non-uniformities in the response of the actual scintillator material and/or photo-detectors employed, more widely applicable detector response functions may be provided. While the use of more generic detector response functions does not provide the maximum possible improvement in energy resolution, it does provide a way to quickly and easily improve the performance of a large number of similarly configured gamma-ray systems without requiring individual calibration.

Another way to obtain more generic detector response functions for a particular gamma-ray camera imager configuration would be to determine the average of a number of previously determined detector response functions seen in examples of the imager configuration of interest.

REFERENCES

[1] H. O. Anger, Rev. Sci. Instru. 29, 27 (1958)
[2] K. B. Parnham, R. K. Davies, S. Vydrin et al., 'Development, design and performance of a CdZnTe-based nuclear medical imager', J. Nuclear Medicine 43(5) 935 Supplement S (May 2002)
[3] L. J. Meng, D. Ramsden, 'Inter-comparison of three algorithms for gamma-ray spectral deconvolution', IEEE Trans. Nuclear Science 47, 1329-1336 (2000)
[4] L. J. Meng, D. Ramsden, V. M. Chirkin, V. N. Potapov, O. P. Ivanov, 'Design and performance of a large volume spherical scintillation detector for gamma-ray spectroscopy', Nuclear Instruments & Methods, A485, 468-476 (2002)
[5] L. J. Meng, D. Ramsden, V. M. Chirkin, V. N. Potapov, O. P. Ivanov, S. N. Ignatov, 'Scintispheres—the shape of things to come in gamma-ray spectroscopy', Accepted for publication in IEEE Trans. Nuclear Science (2002)
[6] U.S. Pat. No. 5,903,008
[7] U.S. Pat. No. 5,530,248
[8] U.S. Pat. No. 5,633,499
[9] U.S. Pat. No. 5,561,297
[10] M. J. Berger and S. M. Seltzer, 'Response function for Sodium Iodide scintillation detectors', Nuclear Instruments & Methods, A104, 317-332 (1972)

What is claimed is:

1. A gamma-ray camera system comprising:
    a gamma-ray imager including detector pixels formed from a scintillator material;
    a detector read-out component for determining positions and energies of scintillation events occurring within the scintillator material;
    an energy spectra accumulating component for compiling observed energy spectra of scintillation events in the detector pixels; and
    a spectra processing component operable to deconvolve a pixel-specific detector spectral response function from the observed energy spectra for providing improved energy resolution, wherein different spectral processing is applied for different scintillation events according to the location of the different scintillation events in the scintillator material.

2. A gamma-ray camera system according to claim 1, wherein the detector spectral response functions are selected from a store of detector spectral response functions which include detector spectral response functions specific to individual detector pixels.

3. A gamma-ray camera system according to claim 1, wherein the detector spectral response functions are selected from a store of detector spectral response functions which comprises a family, and for the pixels in the gamma-ray image a detector spectral response function is selected from the family.

4. A gamma-ray camera system according to claim 1, wherein the scintillator material comprises a single scintillator crystal optically coupled to a plurality of photo-detectors.

5. A gamma-ray camera system according to claim 1, wherein the scintillator material comprises an array of discrete scintillator crystal elements optically coupled to a corresponding array of discrete photo-detectors.

6. A gamma-ray camera system according to claim 1, wherein the scintillator material is thallium doped sodium iodide.

7. A method of processing energy spectra recorded in detector pixels of a gamma-ray scintillation camera comprising:
    providing observed energy spectra recorded in the detector pixels; and
    deconvolving a pixel specific detector spectral response function from the observed energy spectra for providing improved energy resolution, wherein different spectral processing is applied for different scintillation events according to the location of the different scintillation events in a scintillator material.

8. A method of processing energy spectra according to claim 7, wherein the detector spectral response functions are selected from a store of detector spectral response functions which include a detector spectral response function specific to individual detector pixels.

9. A method of processing energy spectra data according to claim 7, wherein the detector spectral response functions are selected from a store of detector spectral response functions which comprises a family, and for the detector pixels a detector spectral response function is selected from the family.

10. A gamma-ray camera system comprising:
    a spectra processing component; and
    a data storage component for storing a computer program, said computer program being adapted to implement a method of processing energy spectra recorded in detector pixels of a gamma-ray scintillation camera and to perform the steps of:
        obtaining observed energy spectra recorded in the detector pixels; and
        deconvolving a pixel specific detector spectral response function from the observed energy spectra for providing improved energy resolution, wherein different spectral processing is applied for different scintillation events according to the location of the different scintillation events in a scintillator material.

11. The gamma-ray camera system of claim 10, wherein said computer program is further adapted to select said pixel specific detector spectral response function from a store of detector spectral response functions which comprises a family.

12. A method of generating pixel-specific detector spectral response functions for a gamma-ray imager including detector pixels formed from a scintillator material comprising:
    obtaining a theoretical component to the detector spectral response as a function of detector pixel by performing a simulation;
    obtaining an empirical component to the detector spectral response as a function of detector pixel by observing the spectral response of the gamma-ray imager to a calibration source; and
    combining the theoretical and empirical components to provide detector spectral response functions which are specific to detector pixels and can be used to improve enemy resolution, wherein a first one of the detector spectral response functions is applied to a first scintillation event at a first location in the scintillator material and a second one of the detector spectral response functions is applied to a second scintillation event at a second location in the scintillator material.

13. A gamma-ray camera system comprising:
    a spectra processing component; and
    a data storage component for storing a computer program, said computer program being adapted to implement a method of generating pixel specific detector spectral response functions for a gamma-ray imager including detector pixels formed from a scintillator material and to perform the steps of:

obtaining a theoretical component to the detector spectral response as a function of detector pixel by performing a simulation;

obtaining an empirical component to the detector spectral response as a function of detector pixel by observing the spectral response of the gamma-ray imager to a calibration source; and combining the theoretical and empirical components to provide detector spectral response functions which are specific to detector pixels and can be used to improve enemy resolution, wherein a first one of the detector spectral response functions is applied to a first scintillation event at a first location in the scintillator material and a second one of the detector spectral response functions is applied to a second scintillation event at a second location in the scintillator material.

14. A gamma-ray camera system comprising:

a spectral processing component; and a data storage component for storing a computer program and detector spectral response functions, said detector response functions being calculated according to a method of generating pixel-specific detector spectral response functions for a gamma-ray imager including detector pixels formed from a scintillator material, said computer program being adapted to perform the steps of:

obtaining a theoretical component to the detector spectral response as a function of detector pixel by performing a simulation;

obtaining an empirical component to the detector spectral response as a function of detector pixel by observing the spectral response of the gamma-ray imager to a calibration source; and combining the theoretical and empirical components to provide detector spectral response functions which are specific to detector pixels and can be used to improve enemy resolution, wherein a first one of the detector spectral response functions is applied to a first scintillation event at a first location in the scintillator material and a second one of the detector spectral response functions is applied to a second scintillation event at a second location in the scintillator material.

15. The gamma-ray camera system of claim 10, wherein said computer program is further adapted to select said pixel specific detector spectral response function from a store of detector spectral response functions.

* * * * *